(12) United States Patent
Bang et al.

(10) Patent No.: US 6,530,890 B2
(45) Date of Patent: Mar. 11, 2003

(54) ULTRASOUND DIAGNOSTIC APPARATUS AND METHOD FOR MEASURING BLOOD FLOW VELOCITY USING DOPPLER EFFECT

(75) Inventors: Ji Hoon Bang, Anyang-si (KR); Cheol An Kim, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 0 days.

(21) Appl. No.: 09/899,009

(22) Filed: Jul. 3, 2001

(65) Prior Publication Data

US 2002/0016547 A1 Feb. 7, 2002

(30) Foreign Application Priority Data

Jul. 8, 2000 (KR) ........................................ 2000-39084

(51) Int. Cl.7 .................................................. A61B 5/02
(52) U.S. Cl. ........................ 600/504; 600/454; 600/455
(58) Field of Search ................................. 600/300–301, 600/454–457, 481, 504

(56) References Cited

U.S. PATENT DOCUMENTS 5,606,972 A * 3/1997 Routh ........................ 600/455
5,634,465 A * 6/1997 Schmiesing et al. ........ 600/454
5,868,676 A * 2/1999 McCabe et al. ............ 600/454
6,050,948 A * 4/2000 Sasaki et al. ............... 600/453
6,251,077 B1 * 6/2001 Mo et al. .................... 600/455

* cited by examiner

Primary Examiner—Robert L. Nasser
Assistant Examiner—Patricia Mallari
(74) Attorney, Agent, or Firm—Wiggin & Dana LLP; Dale L. Carlson; Michael K. Kinney

(57) ABSTRACT

An ultrasound diagnostic apparatus and method for measuring a blood flow velocity effectively select one of the positive frequency range and the negative frequency range to compute noise threshold, and determine a reliability of the computed noise threshold. A sample data generator samples a reflected signal of the ultrasound signal transmitted into a human body. A frequency distribution data generator processes the sample data, and generates a frequency distribution data including a number of frequency components. A first determiner selects one of a positive frequency range and a negative frequency range of the frequency distribution data. A second determiner determines a noise threshold by using a predetermined number of frequency components within the frequency range selected by the first determiner. A third determiner determines a peak frequency component having the highest frequency among the frequency components. Each frequency component has a power level higher than the noise threshold, and the peak frequency component corresponds to the peak blood frequency velocity.

10 Claims, 5 Drawing Sheets

ULTRASOUND DIAGNOSTIC APPARATUS AND METHOD FOR MEASURING BLOOD FLOW VELOCITY USING DOPPLER EFFECT

FIELD OF THE INVENTION

The present invention relates to an ultrasound diagnostic system for measuring blood flow velocity using Doppler effect. In particular, the invention relates to an apparatus and method for measuring peak value and mean value of blood flow velocity.

BACKGROUND OF THE INVENTION

An ultrasonic diagnostic system using the Doppler effect is widely used in measuring the velocity of blood flow in the human body. In such a system, an ultrasonic transducer array transmits an ultrasonic signal toward a moving object, e.g., red blood cells, and receives a reflected signal from the object. The system computes the frequency shift or phase shift of the reflected signal with respect to the transmitted signal in order to determine the velocity of the moving object.

FIG. 1 is a block diagram of a conventional ultrasound diagnostic apparatus 10 for measuring the velocity of blood flow in a human body. The apparatus 10 comprises a transducer array 103, a pre-amplifier 104, a time-variable gain compensator (TGC) amplifier 105, an analog-to-digital (A/D) converter 106, a quadrature demodulator 107, a digital signal processor 108, a display device 109, and a peak blood flow velocity detector 110.

The transducer array 103 transmits an ultrasound signal to an object (not shown), e.g., red blood cells in a human body, and receives a reflected signal from the object (not shown) possibly with noise. The received signal is inputted to the pre-amplifier 104 for amplification. The output of the pre-amplifier 104 is amplified at the TGC amplifier 105 with a time-varying gain in order to compensate attenuation due to propagation distance of the ultrasound signal in the human body. The output of the TGC amplifier 105 is converted to a digital signal at A/D converter 106. The digital signal is demodulated at a quadrature demodulator 107. The demodulated signal is applied to the digital signal processor 108 where the velocity of the object (not shown) is computed. The velocity is displayed at the display device 109 for human users.

In the digital signal processor 108, the demodulated signal undergoes clutter filtering, fast Fourier transforming (FFT) and post-processing to obtain the velocity distribution spectrum. That is, the clutter that is reflected from slowly moving organ and muscle compared to the blood is removed from the demodulated signal by a high-pass filter. Then, the frequency distribution data of 2N frequency components are generated from the filtered signal by using a well known FFT technique. Finally, as post-processing, a known signal processing such as the log compression and base line shifting are performed on the frequency distribution data corresponding to the velocity distribution spectrum.

It is desirable to measure the mean velocity and the peak velocity of the blood flow because blood flow is actually a collection of many blood cells that do not move uniformly in one direction. In other words, at one instant of time, blood cells exhibit different moving velocities and moving directions. As a result, when an ultrasonic signal of a given frequency is transmitted to these cells, its returned ultrasonic signal received from the cells would be composed of many different frequencies around the given frequency because these different velocities would bring about different Doppler frequency shifts. In addition, the received ultrasonic signal inevitably includes noise in addition to an ideally reflected signal from the object. The noise, of course, should be isolated from the total reflected signal components to accurately determine the mean and peak velocities of the blood flow. Typically, to isolate the noise from the reflected signal, a noise threshold is established so that frequency components of the received signal whose power levels are below could be discarded as noise.

FIG. 2 is a frequency distribution of the received ultrasonic signal from a targeted blood flow. Note that the center frequency has been shifted to zero in order to graphically illustrate the directions of blood cells. Frequency components in the negative domain represent frequency shifts of the ultrasonic signal that reflected off blood cells that move away from the transducer. Conversely, those in the positive domain represent frequency shifts of the ultrasound that reflected off those blood cells that move toward the transducer. It is well known in the art that, if a frequency shift is detected, then the velocity of a moving object that caused the shift can be computed as they are proportional to each other. In the graph of FIG. 2, a velocity corresponding to $f_p$ is considered as the peak velocity because $f_p$ is farthest from the center frequency (thus being greatest frequency shift) and its power is above the noise threshold. The peak velocity is detected at the peak blood flow velocity detector 110. The mean velocity is obtained by computing the mean of all the velocities corresponding to the frequency components whose power levels are above the noise threshold.

As described above, it is important to accurately determine the noise threshold, i.e., the power level that discriminates between the noise and the purely reflected signal, in the computation of the mean and peak velocities of the blood flow. One of known methods for determining a noise threshold is to use the mean power of frequency components in a selected frequency range far higher than the transmitted frequency, i.e., in a frequency range where no reflected frequency components are expected. For example, the mean of power levels of highest frequencies from the frequency distribution of a received signal was used as the noise threshold. The hypothesis behind this conventional method is that random noise tends to have a flat power spectrum so that the power levels of frequencies where desired signals are not present would be that of the noise.

SUMMARY OF THE INVENTION

It is, therefore, an objective of the present invention to provide an ultrasound diagnostic apparatus for measuring blood flow velocity and method thereof, capable of selecting effectively one of the positive frequency range and the negative frequency range to compute noise threshold.

In accordance with one aspect of the present invention, there is provided an ultrasound diagnostic apparatus for measuring blood flow velocity and method thereof, capable of determining reliability of the computed noise threshold.

In order to achieve this objective, an ultrasound diagnostic apparatus for measuring a blood flow velocity includes: means for generating sample data by transmitting an ultrasound signal into a human body and sampling a reflected signal of the ultrasound signal; means for generating frequency distribution data by processing the sample data, wherein the frequency distribution data includes a number of frequency components, each of the frequency components having a corresponding power level; first determining means for selecting one of a positive frequency range and a negative frequency range of the frequency distribution data; second determining means for determining a noise threshold by using a predetermined number of frequency components within the frequency range selected by the first determining means; and third determining means for determining a peak frequency component having a highest frequency among the frequency components, each having a power level higher than the noise threshold and the peak frequency component corresponding to the peak blood flow velocity.

An ultrasound diagnostic method for measuring a blood flow velocity, the method includes the steps of: (a) generating sample data by transmitting an ultrasound signal into a human body and sampling a reflected signal of the ultrasound signal; (b) generating frequency distribution data by processing the sample data, wherein the frequency distribution data includes a number of frequency components, each of the frequency components having a corresponding power level; (c) selecting one of a positive frequency range and a negative frequency range of the frequency distribution data; (d) determining a noise threshold by using a predetermined number of frequency components within the frequency range selected at step (c); and (e) determining peak frequency component having a highest frequency among the frequency components, each having a power level higher than the noise threshold and the peak frequency component corresponding to the peak blood flow velocity.

BRIEF DESCRIPTIONS OF THE DRAWINGS

The above and other objects and features of the present invention will become apparent from the following description of preferred embodiments given in conjunction with the accompanying drawings, in which.

Figure 1:
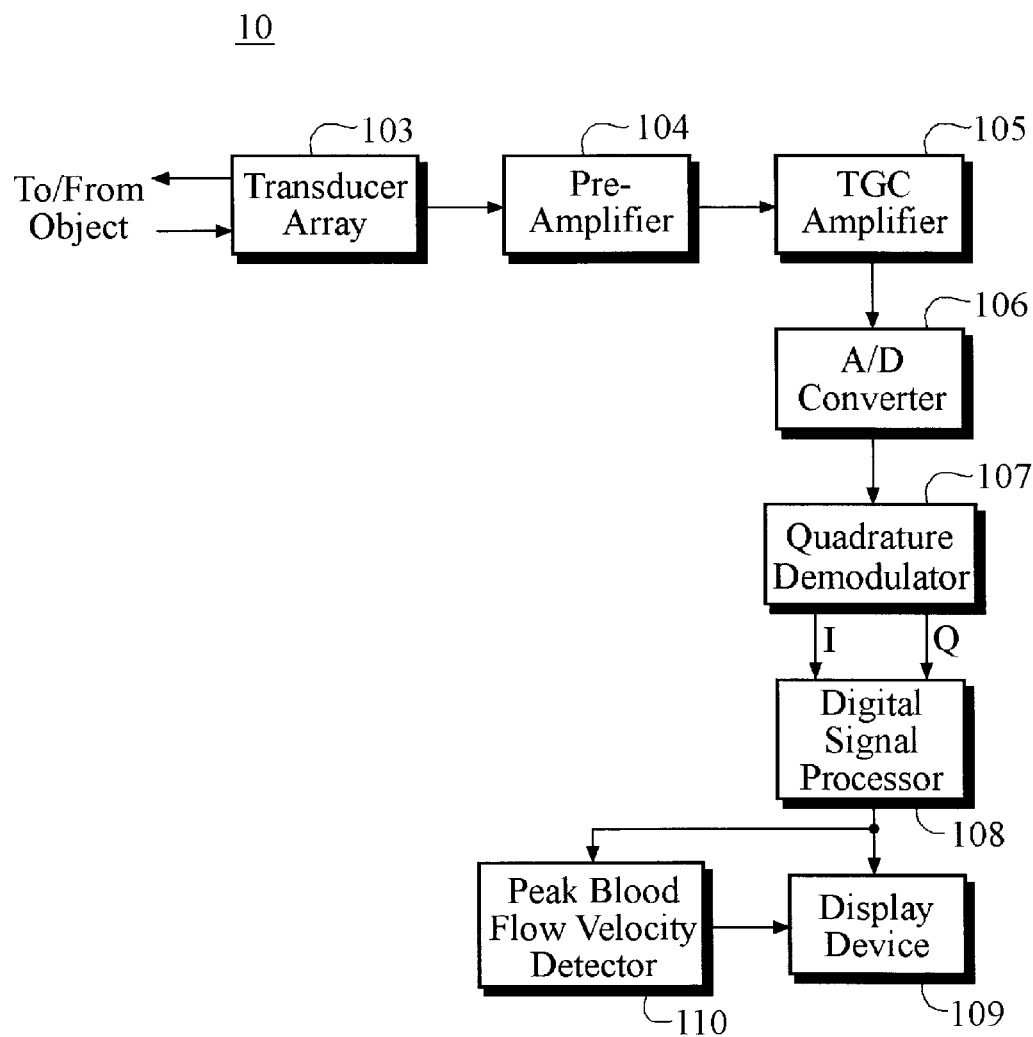
FIG. 1 shows a block diagram of a conventional ultrasound diagnostic apparatus for measuring blood flow velocities.
Figure 2:
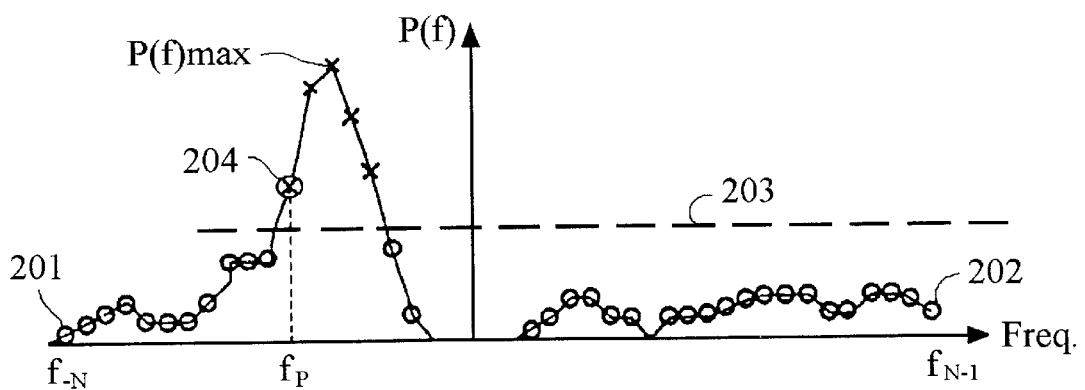
FIG. 2 illustrates the frequency distribution of a received ultrasonic signal.
Figure 3:
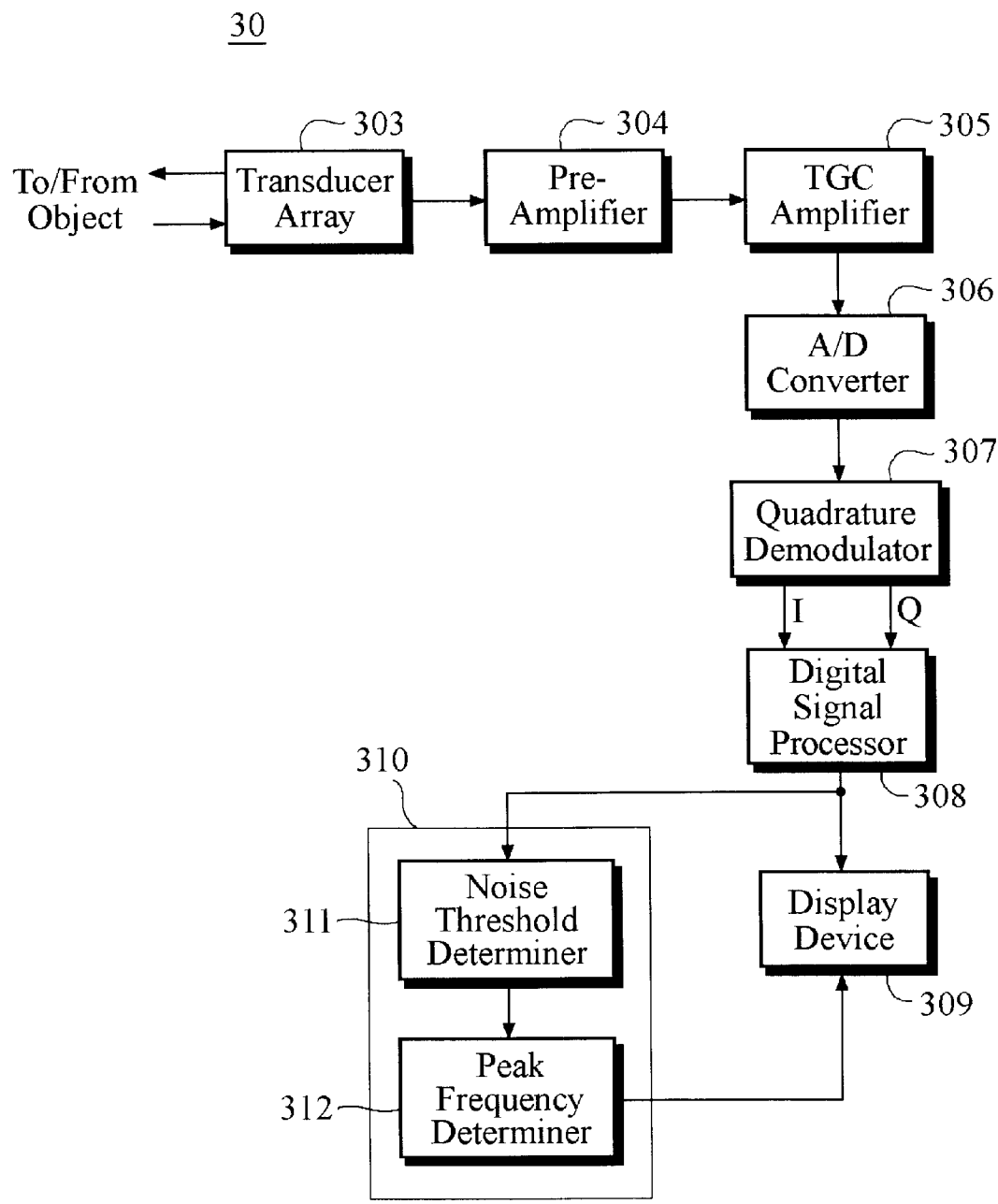
FIG. 3 is a block diagram of an ultrasound diagnostic apparatus for measuring blood flow velocities according to the present invention.
Figure 4:
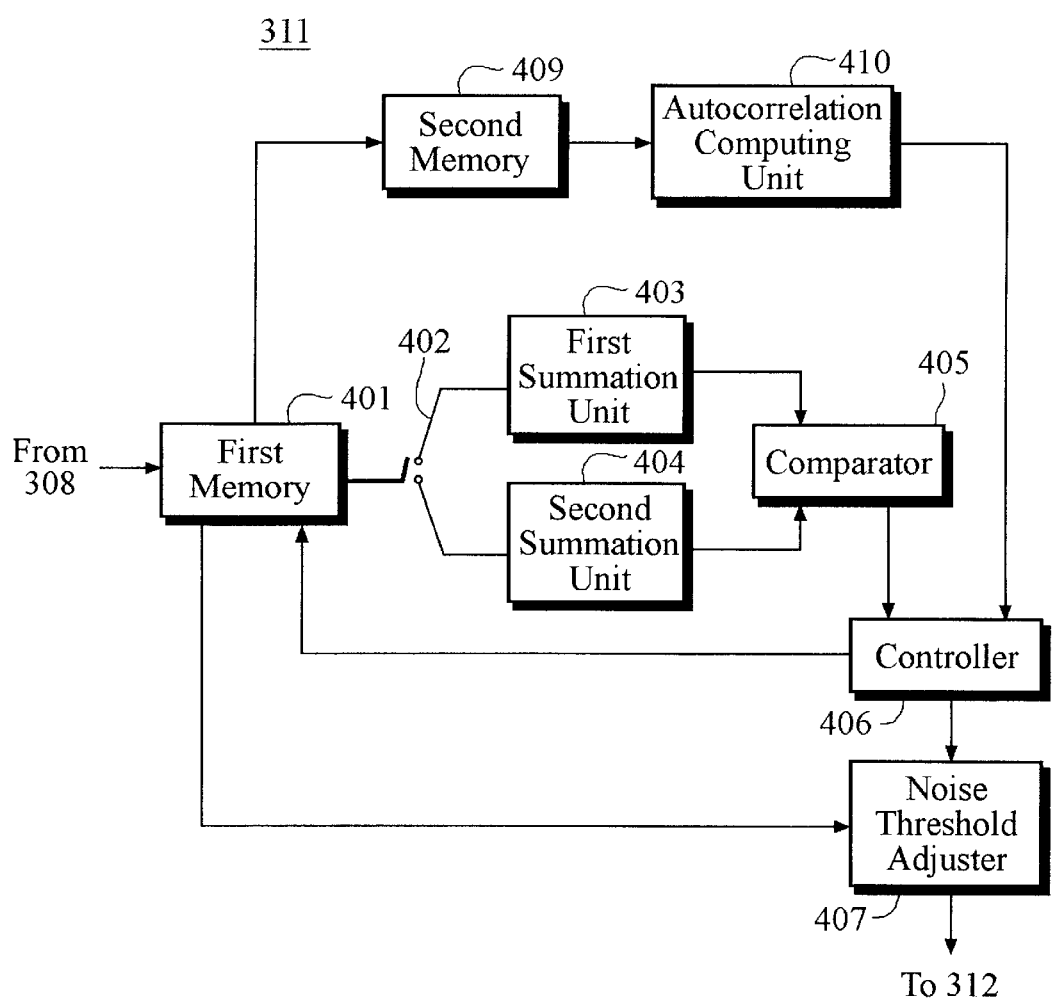
Figure 5:
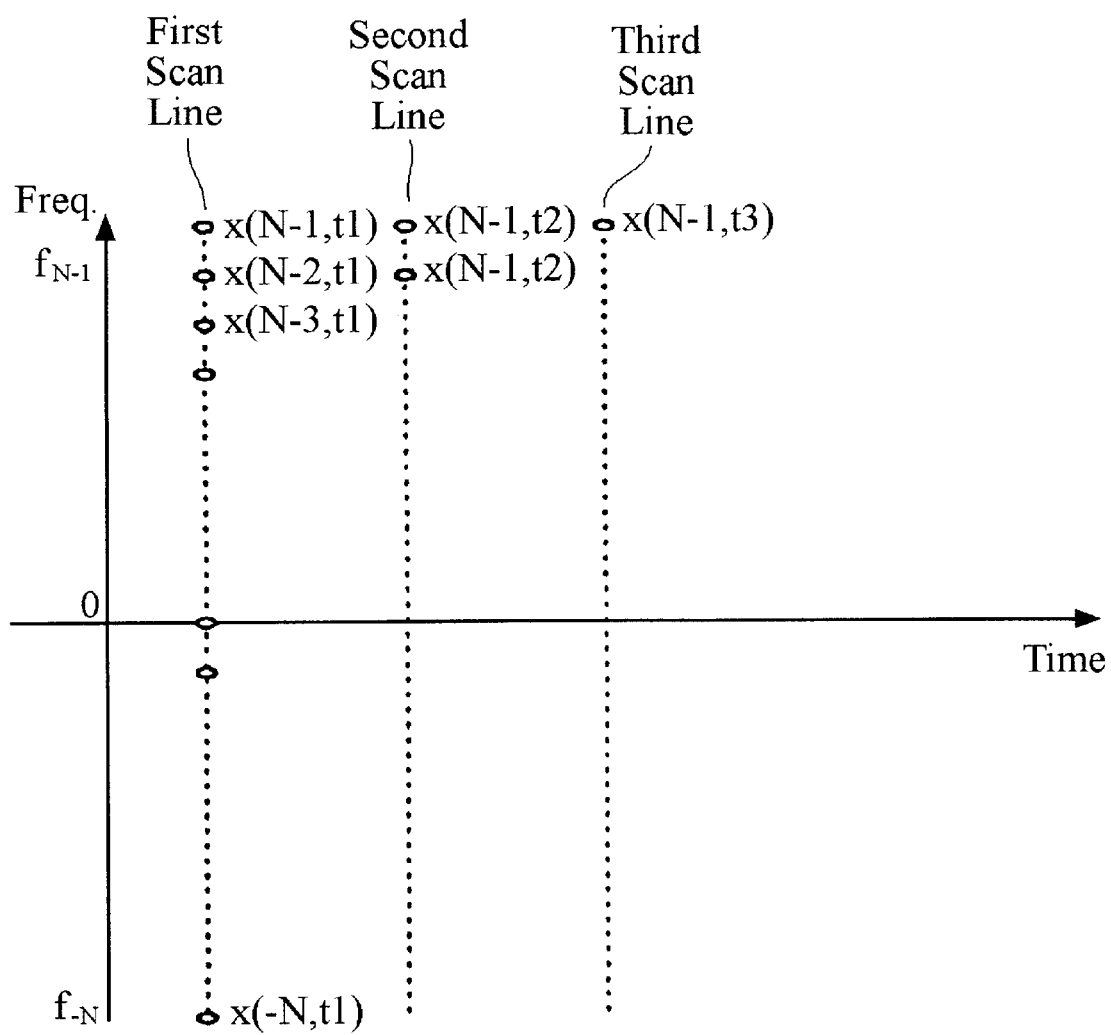

FIG. 4 provides a block diagram of the noise threshold determiner of FIG. 3; and FIG. 5 is a graph displaying the frequency distribution data at a few instants of time.

DETAILED DESCRIPTION OF THE PRESENT INVENTION

An embodiment of the present invention will now be described in details in reference to the accompanying drawings.

FIG. 3 is a block diagram of an ultrasound diagnostic apparatus for measuring blood flow velocities according to the present invention.

As shown in FIG. 3, the ultrasound diagnostic system 30 comprises a transducer array 303, a pre-amplifier 304, a time-variable gain compensator (TGC) amplifier 305, an analog-to-digital (A/D) converter 306, a quadrature demodulator 307, a digital signal processor 308, a display device 309, and a peak blood flow velocity detector 310. In other words, the present invention starts to differ from the prior art system in at least providing a device and method for determining the valid peak and mean velocities of blood flow.

The peak blood flow velocity detector 310 comprises a noise threshold determiner 311 and a peak frequency determiner 312. The noise threshold determiner 311 determines a noise threshold value on the basis of 2N frequency distribution spectrum data. The peak frequency determiner 312 selects a frequency of the largest absolute value among a plurality of frequency components having the power level beyond the noise threshold value determined by the noise threshold determiner 311, and determines the selected frequency as a peak frequency indicating a peak blood flow velocity.

According to the method for determining the noise threshold of the present invention, it is first determined whether positive or negative frequency components among the 2N frequency distribution spectrum will be used as a basis for determining a threshold. The determination depends on the result of a comparison between the sum of the powers levels of all the positive frequency components and that of all the negative frequency components. Here, the positive frequency components are those frequency components of a reflected ultrasonic signal that are higher than the frequency of a transmitted ultrasonic signal. Likewise, the negative frequency components are those frequency components of a reflected ultrasonic signal that are lower than the frequency of the transmitted ultrasonic signal. If the power sum for the positive frequency components is greater than that for the negative frequency components, a noise threshold is derived using the negative frequency components because it is assumed that the noise in the negative domain is not "contaminated" by significant signal components. In other words, the negative frequency components are presumed to be due to noise alone.

FIG. 4 shows a block diagram of the noise threshold determiner 311 embodying to the above-mentioned aspect of the present invention. The noise threshold determiner 311 is comprised of a first memory 401, a switch 402, a first summation unit 403, a second summation unit 404, a comparator 405, a controller 406, a noise threshold adjuster 407, a second memory 409 and an autocorrelation computing unit 410. The first memory 401 stores 2N frequency components obtained by Fourier transforming demodulated received signal samples. The first memory 401 provides the positive components and negative components to the first and second summation units 403, 404 respectively via the switch 402 under control of the controller 406. As a result, the first summation unit 403 adds together the power levels of N positive frequency components while the second summation unit 404 adds together the power levels of N negative frequency components. The comparator 405 compares the two sums received from the summation units 403, 404 and provides the controller 406 with the comparison result. If the sum from the first summation unit 403 is greater than that from the second summation unit 404, the controller 406 determines that the reflected signal exists in the positive frequency domain while only the noise exists in the negative frequency domain. In this case, it reads out from the first memory 401 a predetermined number (L) of negative frequency components to the noise threshold adjuster 407, L being a positive integer smaller than N. In other words, L highest negative frequency components are provided. The noise threshold adjuster 407 computes the mean of the power levels of the negative L frequency components as the noise threshold. On the other hand, if the sum from the first summation unit 403 is smaller than that from the second summation unit 404, L highest positive frequency components instead will be selected in the determination of a noise threshold. Based on thus determined noise threshold, the peak frequency determiner 312 selects the peak frequency. Specifically it selects the greatest frequency component among those positive frequencies whose power levels are above the threshold. As known in the art, the peak frequency corresponds to the frequency shift of the reflected ultrasonic signal due to the fastest moving blood cells. Similarly the mean blood flow velocity is computed by using the frequency components whose powers are above the noise threshold. As describe above, because the present invention ensures that a noise threshold is determined using only noise components, the mean and peak velocities of blood flow computed based on purely reflected signal components are more accurate than those obtained by the prior art systems.

FIG. 5 is a graph displaying the frequency distribution of a reflected ultrasonic signal at each instant of time on a display device 309 of the ultrasound diagnostic apparatus 30. Here, each of scan lines is a graphical representation of 2N frequency distribution data of the reflected ultrasonic signal at an instant of time. For example, an M-th scan line represents a set of 2N frequency components obtained at a particular time $t_M$. The power level of a frequency $f_i$ on the M-th scan line is here denoted by $x(i, t_m)$ and usually indicated on the display screen in gray scale. The higher the power level is the brighter the point is. By definition, $x(i, t_M)$ also represents a velocity of the blood flow at time $t_M$.

The noise threshold for each scan line can ascertained as described below, further increasing the confidence of the peak and mean blood flow velocities at each instant time. Specifically the reliability of a noise threshold for each instant time can be evaluated taking advantage of the random nature of noise. Because of this random nature, noise has very low autocorrelation. According to an aspect of the present invention, a second memory 409 stores a set of L frequency components that were used to compute the noise threshold for the M-th scan line. It also stores a set of L frequency components for the scan line adjacent to the M-th scan line. An autocorrelation computing unit 410 computes autocorrelation between the two sets of L frequency components. If the autocorrelation is below a predetermined value, the set of L frequencies are presumed to have stemmed from noise and thus could be used to compute a noise threshold. Otherwise, the L frequency components are considered to include some signal components and thus are not proper for the determination of a noise threshold. In this case an established noise threshold for other scan line, e.g., the (M−1)-th scan line is used instead.

The autocorrelation computing unit 410 uses the following equation to determine the autocorrelation $\simeq$.

$$\rho = \frac{\frac{1}{L}\sum_{i=N-L}^{N-1} x(f_i, t_M)x(f_i, t_{M+1})}{\sqrt{\frac{1}{L}\sum_{i=N-L}^{N-1} x(f_i, t_M)^2}\sqrt{\frac{1}{L}\sum_{i=N-L}^{N-1} x(f_i, t_{M+1})^2}}$$

Eq.(1)

Note that L frequency components ranging from the (N−L)-th frequency to (N−1)-th frequency in the positive frequency domain are used. If the sum of the power levels of the positive frequency components were greater than that of the negative frequency components, the autocorrelation would be computed by L frequency components ranging from (−N)-th frequency to (−N+L−1)-th frequency in the negative frequency range. The controller 406 controls the noise threshold adjuster 407 either to raise or lower the threshold depending on the reliability of a noise threshold. For example, if the autocorrelation is too high, it directs the noise threshold adjuster 407 to set the noise threshold at another level, i.e., to a level that was previously confirmed as reliable.

Accordance with the present invention, the high frequency range used to compute the noise threshold can be selected effectively between the positive frequency range and the negative frequency range. And, in the present invention, the reliability of the noise threshold can be evaluated.

While there has been described and illustrated system and method for measuring peak and mean velocities of the blood flow by using the spectral Doppler technology, it will be apparent to those skilled in the art that variations and modifications are possible without deviating from the broad principles and teachings of the present invention which should be limited solely by the spirit and scope of the claims appended hereto.

What is claimed is:

1. An ultrasound diagnostic apparatus for measuring a blood flow velocity, the apparatus comprising:

means for generating sample data by transmitting an ultrasound signal into a human body and sampling a reflected signal of the ultrasound signal;

means for generating frequency distribution data by processing the sample data, wherein the frequency distribution data includes a number of frequency components, each of the frequency components having a corresponding power level;

first determining means for selecting one of a positive frequency range and a negative frequency range of the frequency distribution data;

second determining means for determining a noise threshold by using a predetermined number of frequency components within the frequency range selected by the first determining means; and third determining means for determining a peak frequency component having a highest frequency among the frequency components, each having a power level higher than the noise threshold and the peak frequency component corresponding to the peak blood flow velocity;

wherein the first determining means determines the frequency range selected by the first determining means by selecting a frequency range having the largest sum of power levels of the frequency components between the positive frequency range and the negative frequency range.

2. The apparatus of claim 1, further comprising:

fourth determining means for determining a mean blood flow velocity from the frequency distribution data by using the noise threshold.

3. The apparatus of claim 1, wherein the second determining means includes means for evaluating the reliability of the noise threshold.

4. The apparatus of claim 3, wherein the evaluating means includes means for computing a correlation between the predetermined number of frequency components at a first and a second predetermined time, and means for determining whether reliability of the noise threshold at the first predetermined time is lower than a first predetermined value if the correlation is higher than a second predetermined value.

5. The apparatus of claim 4, wherein, when the reliability of the noise threshold at the first predetermined time is determined to be lower than the first predetermined value, the peak frequency component at the first predetermined time is determined depending another noise threshold that is determined at a time other than the first predetermined time and has reliability which equals to or larger than the predetermined extent.

6. An ultrasound diagnostic method for measuring a blood flow velocity, the method comprising the steps of:
  (a) generating sample data by transmitting an ultrasound signal into a human body and sampling a reflected signal of the ultrasound signal;
  (b) generating frequency distribution data by processing the sample data, wherein the frequency distribution data includes a number of frequency components, each of the frequency components having a corresponding power level;
  (c) selecting one of a positive frequency range and a negative frequency range of the frequency distribution data;
  (d) determining a noise threshold by using a predetermined number of frequency components within the frequency range selected at step (c); and
  (e) determining peak frequency component having a highest frequency among the frequency components, each having a power level higher than the noise threshold and the peak frequency component corresponding to the peak blood flow velocity;
  wherein step (c) includes the step of (cl) selecting the frequency range by selecting a frequency range having the smaller sum of power levels of the frequency components between the positive frequency range and the negative frequency range.

7. The method of claim 6, further comprising the step (f) determining a mean blood flow velocity from the frequency distribution data by using the noise threshold.

8. The method of claim 6, wherein the step (d) includes the step (d1) of evaluating the reliability of the noise threshold.

9. The method of claim 8, wherein the step (d1) includes:
  (d11) computing a correlation between the predetermined number of frequency components at a first and a second predetermined time; and
  (d12) determining whether the reliability of the noise threshold at the first predetermined time is lower than a first predetermined value if the correlation is higher than a second predetermined value.

10. The method of claim 9, wherein the step (e) includes the step of (e1), when the reliability of the noise threshold at the first predetermined time is determined to be lower than the first predetermined value, determining the peak frequency component at the first predetermined time depending another noise threshold that is determined at a time other than the first predetermined time and has reliability which equals to or larger than the predetermined extent.

* * * * *